US00PP34637P2

(12) United States Plant Patent
Bagdasarian et al.

(10) Patent No.: US PP34,637 P2
(45) Date of Patent: Oct. 11, 2022

(54) STRAWBERRY PLANT NAMED 'ASHLEY JAY'

(50) Latin Name: ***Fragaria* x *ananassa***
Varietal Denomination: Ashley Jay

(71) Applicants: Jimmy Haig Bagdasarian, Santa Cruz, CA (US); Nicholas Jack Pinkerton, Redding, CA (US); Travis Stegmeir, Salinas, CA (US)

(72) Inventors: Jimmy Haig Bagdasarian, Santa Cruz, CA (US); Nicholas Jack Pinkerton, Redding, CA (US); Travis Stegmeir, Salinas, CA (US)

(73) Assignee: Lassen Canyon Nursery, Inc., Redding, CA (US)

( * ) Notice: Subject to any disclaimer, the term of this patent is extended or adjusted under 35 U.S.C. 154(b) by 0 days.

(21) Appl. No.: 17/448,699

(22) Filed: Sep. 23, 2021

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./156, 208, 209
See application file for complete search history.

(56) References Cited

U.S. PATENT DOCUMENTS

| | | | |
|---|---|---|---|
| PP22,472 | P3 | 1/2012 | Bagdasarian |
| PP26,974 | P3 | 7/2016 | Bagdasarian |
| PP27,034 | P3 | 8/2016 | Bagdasarian |
| PP27,190 | P3 | 9/2016 | Bagdasarian |
| PP30,326 | P2 | 4/2019 | Bagdasarian |
| PP30,426 | P2 | 4/2019 | Bagdasarian |
| PP30,427 | P2 | 4/2019 | Bagdasarian |
| PP33,284 | P2 | 7/2021 | Bagdasarian |

*Primary Examiner* — Karen M Redden
(74) *Attorney, Agent, or Firm* — Phase M. Legal

(57) ABSTRACT

A new and distinct variety of strawberry plant (*Fragaria* x *ananassa*) named 'Ashley Jay' is presented here. This new short-day strawberry variety is characterized by moderate vigor plants which produce attractive conical fruit, which has an exceptional, sweet strawberry flavor and a desirable lighter red exterior color. The variety is remontant in cool coastal areas of California, producing high quality fruit all season long.

7 Drawing Sheets

Latin name of the genus and species of the plant claimed: Botanical classification: *Fragaria* x *ananassa.*

Variety denomination: The new strawberry variety denomination is 'Ashley Jay'.

BACKGROUND OF THE INVENTION

Field of Invention

The present invention relates to a new and distinct variety of strawberry named 'Ashley Jay'. This new short-day strawberry variety is the result of a controlled cross in an ongoing breeding program made in 2014. Jimmy Bagdasarian, Nicholas Pinkerton, and Travis Stegmeir are the co-inventors. The variety is botanically known as *Fragaria* x *ananassa.*

The primary market for the 'Ashley Jay' variety is for the fresh market sales of the fruit. 'Ashley Jay' produces high quality, medium to large firm berries, which are attractive, and which have an excellent, sweet flavor. The variety 'Ashley Jay' is remontant in cool, coastal climates, allowing for an extended season.

Comparison With Parent Varieties

The new variety 'Ashley Jay' resulted from a controlled cross conducted in an ongoing breeding program between a strawberry variety designated 'Ruby June', (U.S. Plant Pat. No. 27,190), and a strawberry variety designated '52L32', (Unpatented). The female parent, 'Ruby June', is a short-day variety characterized by a medium-high vigor plant with a semi-upright growth pattern and medium to large conic fruit which have excellent flavor. The fruit of 'Ruby June' has periodic tips and creases, and a medium red exterior and a slightly lighter interior. While it is a short-day plant, 'Ruby June' is considered partially remontant in cool, coastal areas. The male pollen parent '52L32' is day neutral plant, characterized by its large, firm, long conical fruit which have a light red exterior and interior color, and low gloss. Plants of '52L32' are of medium vigor.

The aforementioned controlled cross was carried out in a breeding program at Santa Cruz, Calif., USA. Pollen taken from a '52L32' plant pollinated a female 'Ruby June' plant. The flowers were covered so that no other pollen could contaminate the procedure.

Strawberries developed, were later harvested and the seeds resulting from this cross were extracted and germinated in a greenhouse at Redding, Calif., USA. The resulting seedlings were then transplanted to Shastina, Calif. in 2015, grown for an additional period and allowed to propagate asexually via stolons. Plants were then harvested and planted in breeding test plots in late September in: Oxnard, Calif. (Ventura County); and late October/early November in Watsonville, Calif. (Monterey County). The selection of the new variety was first made in Oxnard, Calif., and designated '143T35'. This selection was later named 'Ashley Jay'.

The new variety was further propagated asexually by stolons in breeding plots in: Macdoel, Calif. (Siskiyou County); and Manteca, Calif. (San Joaquin County). The new variety has also been "meristemed." Small pieces of plant material (approximately 0.5 mm in diameter), consisting of the undifferentiated meristem tissue and one or two leaf primordia, were removed from the buds on crowns of young daughter plants, then placed on nutrient medium, and new plants were grown from them. Planting stock from the "meristemed" plants are growing in a screenhouse located in Redding, Calif.

The propagules of 'Ashley Jay' ('143T35') are identical to the original plant in all distinguishing characteristics; accordingly, the propagation has demonstrated that the traits disclosed herein remain fixed and true to type through successive generations of asexual reproduction.

SUMMARY OF THE INVENTION

'Ashley Jay' is a short-day variety exhibiting the following combination of characteristics, which have been observed repeatedly, and which distinguish this strawberry plant as a new and distinct variety:

1. The variety produces moderate sized fruit;
2. The fruit is generally well shaped conical;
3. The fruit is attractive, having a glossy light red exterior and interior;
4. The fruit is sweet tasting, with exceptional flavor throughout the season;
5. The variety produces a moderate volume of marketable fruit;
6. The plants of the variety are of moderate vigor; and,
7. The variety has shown tolerance to *Fusarium.*

'Ashley Jay' fruit demonstrates characteristics and qualities that are desired by fresh market strawberry sales companies. The lighter, red color is preferred by many shippers of fresh strawberries, as the darker berries are more likely to be viewed as overripe by buyers than are lighter colored berries. 'Ashley Jay' is also a relatively firm berry, which should lend well to a fresh market where shipping is a major factor. The vigor and density of 'Ashley Jay' plants are moderate, with flowers that are at, or extend slightly over the canopy, allowing for adequate pollination. Ripe fruits are mostly easily seen and accessible on the shoulders of the beds allowing for ease of picking.

BRIEF DESCRIPTION OF THE DRAWING

The accompanying color photographs, identified as FIGS. 1 through 7, show the appearance of typical specimens of the new strawberry variety, initially designated '143T35', and now named 'Ashley Jay'. These Figures depict the colors, as nearly true as it is reasonably possible given differences in color illustrations of this character. Accordingly, color in the photographs may differ slightly from the colors discussed in the botanical description. The photographs of the depicted plant, plant parts, and fruit of 'Ashley Jay' were taken in June 2021.

DETAILED BOTANICAL DESCRIPTION OF THE PLANT

Figure 1:
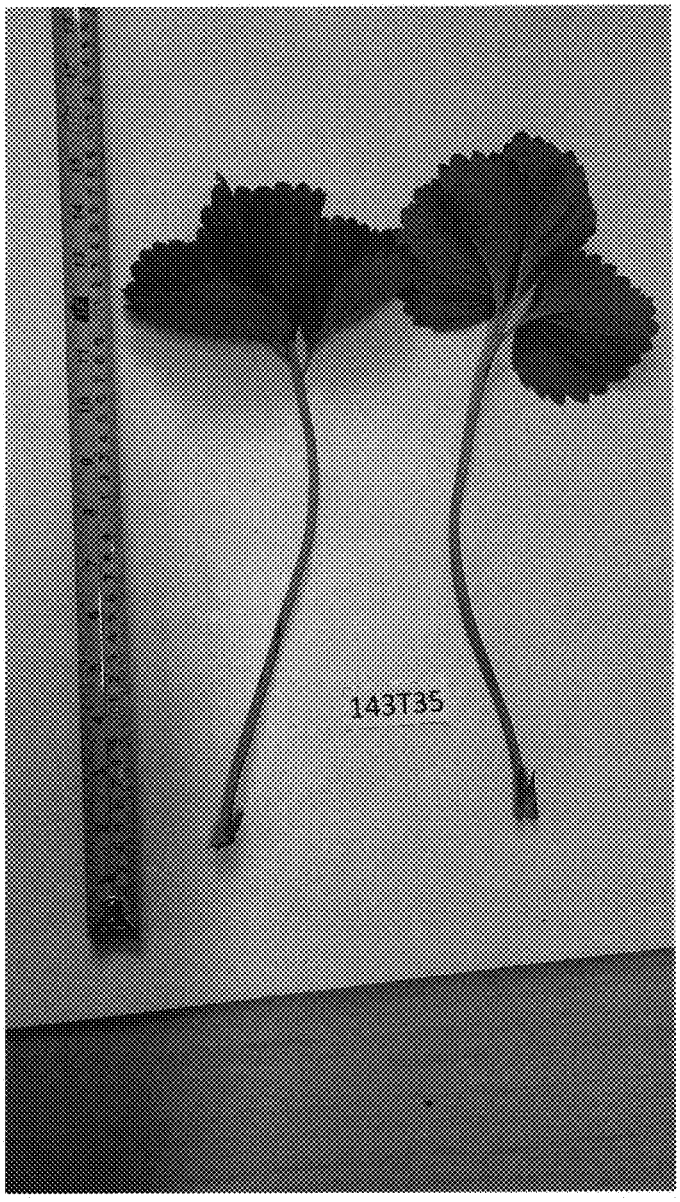
FIG. 1 shows typical leaf and petiole structure at mid-season.
Figure 2:
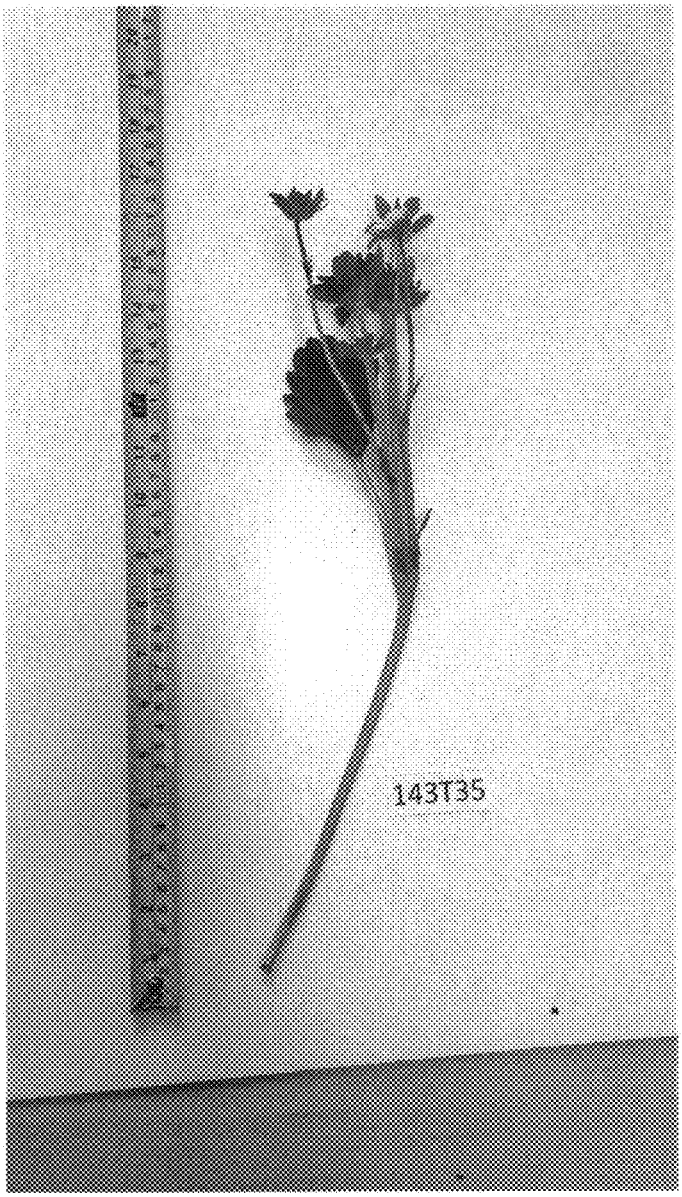
FIG. 2 shows an inflorescence at mid-season.
Figure 3:
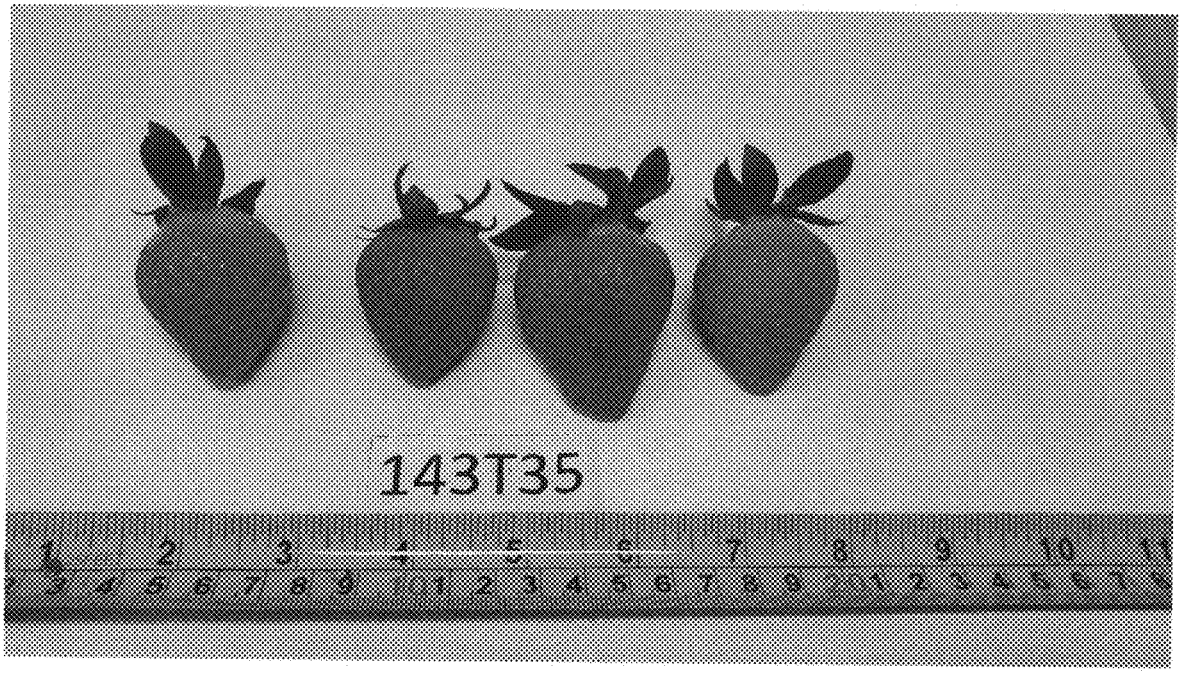
FIG. 3 shows a selection of typical mid-season fruit.
Figure 4:
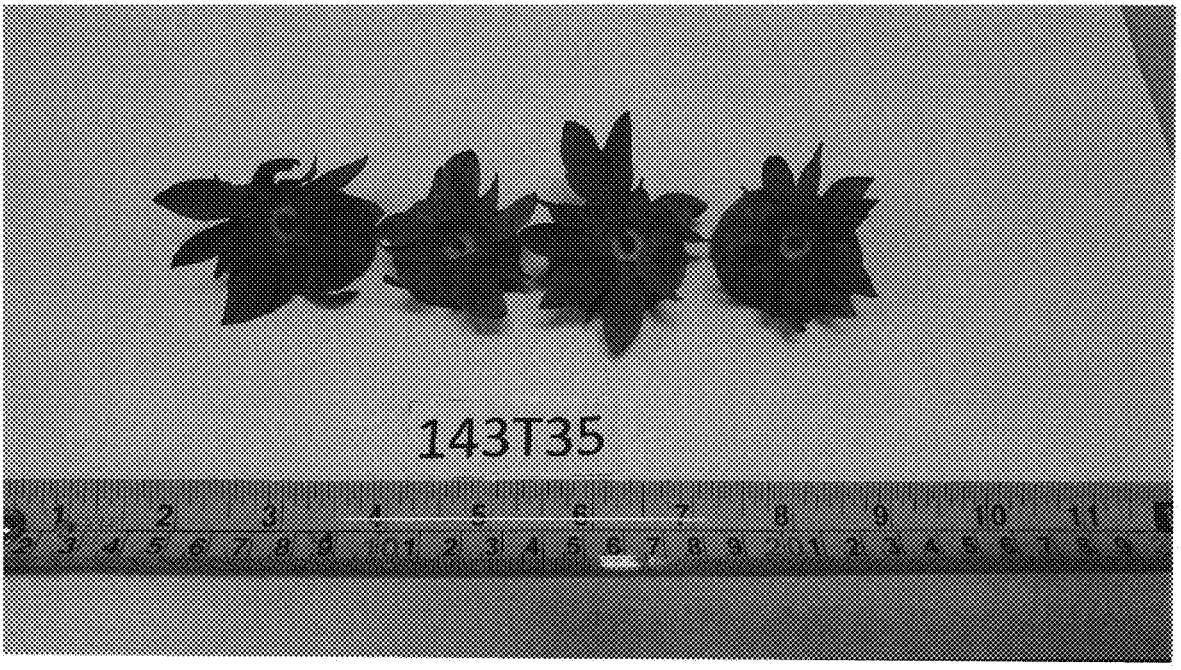
FIG. 4 shows typical calyx position over the berry of 'Ashley Jay'.
Figure 5:
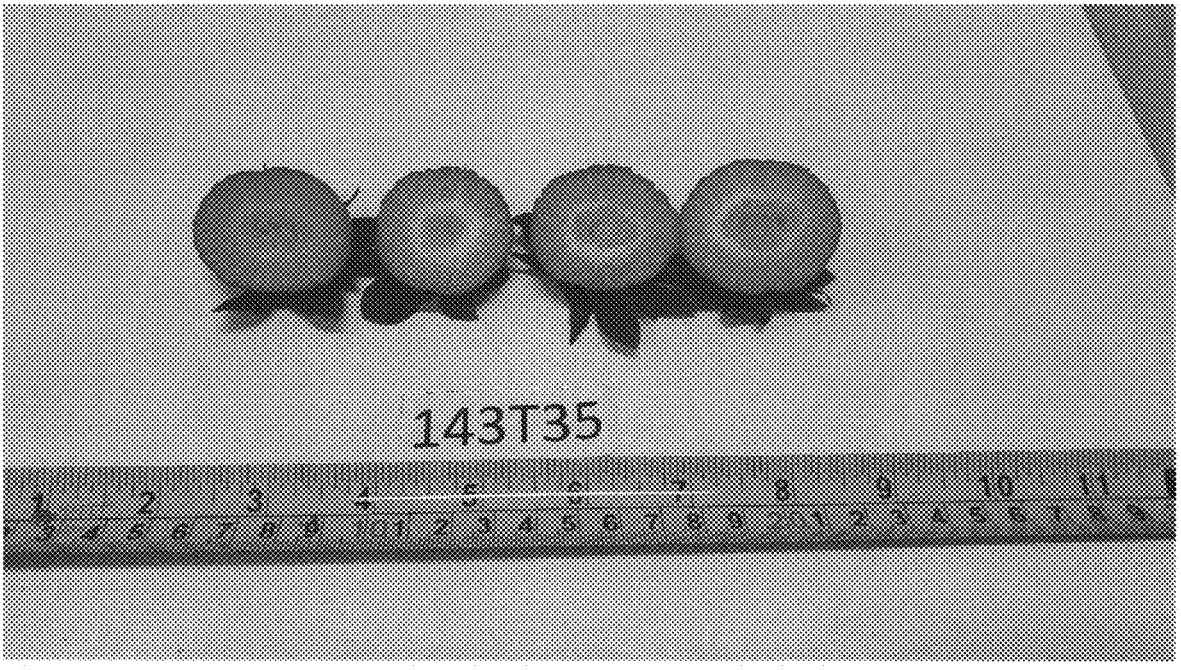
FIG. 5 shows a cross-section of typical fruit internal coloration and core size.
Figure 6:
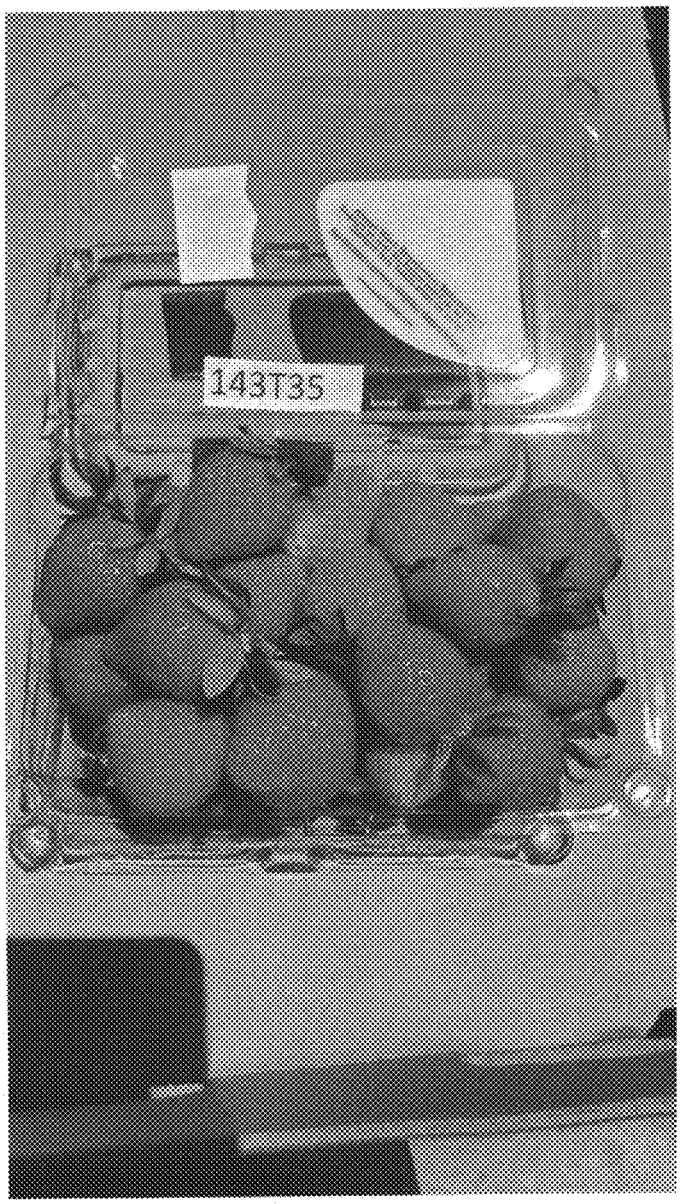
FIG. 6 shows a container of freshly picked fruit.
Figure 7:
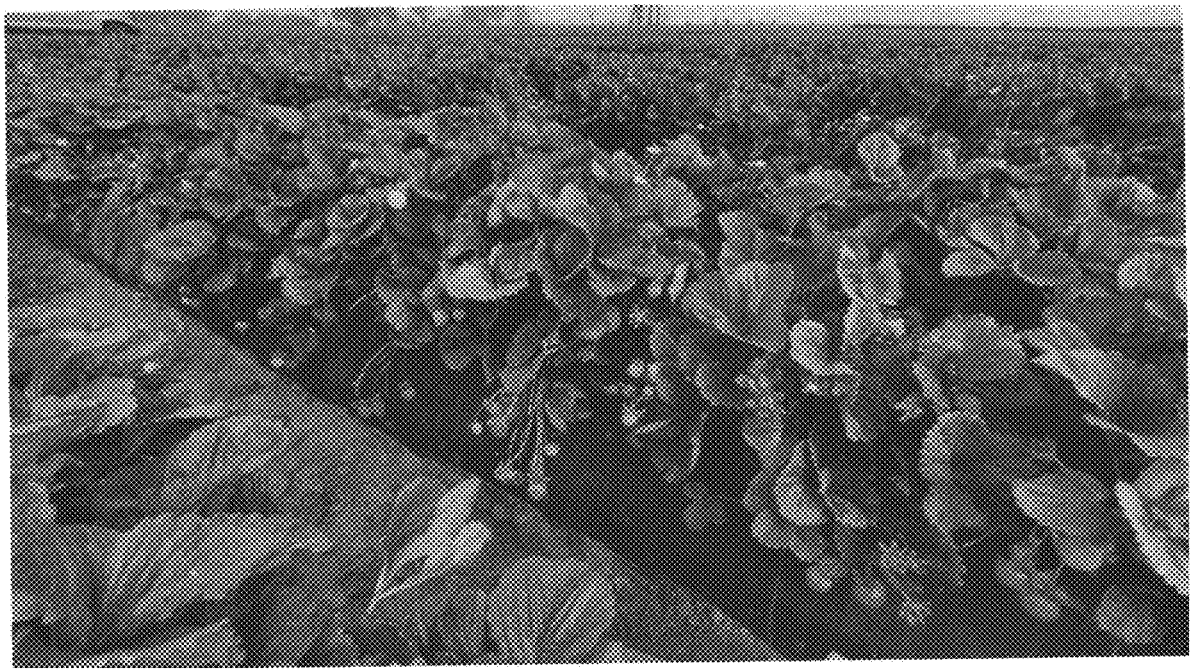
FIG. 7 shows typical plants in a field and position of ripe fruit on the shoulder.

'Ashley Jay' is a new and distinct variety of strawberry, genus and species *Fragaria* x *ananassa*. It is the result of a cross between its female parent, 'Ruby June', and its male parent '52L32'. 'Ruby June' is a short-day variety, while '52L32' is a day neutral variety. 'Ashley Jay' is a short-day variety that has moderate remontant, or ever-bearing, tendencies in temperate coastal environments that are cooler, and is not remontant in hotter inland environments. Plants of 'Ashley Jay' do not bloom continuously in our high elevation nursery, and do not bloom in the heat of our low elevation nursery location in Manteca, Calif., consistent with other short-day varieties. The plants of the new variety have a moderate vigor and produce multiple crowns during the growing season. 'Ashley Jay' exhibits several characteristics which are improvements over one or both of its parent varieties, and other known cultivars. The characteristics of 'Ashley Jay' were observed in plants aged about 7 months from planting in fruiting fields. These characteristics and comparisons with other cultivars are discussed following.

The fruit size of 'Ashley Jay' is moderate, with a seasonal average of 25 g, slightly smaller than its parents. The size of fruit of 'Ashley Jay' is ideal where it is not too large where it could be damaged in containers, but not too small to allow for efficient picking and packing. The fruit of 'Ashley Jay' also hangs down on the shoulder of the bed to allow for more visible fruit and ease of picking. Storability of the fruit has not been measured but in informal observations the fruit retains good physical characteristics and appearance for several days after harvest at room temperature and up to at least a week in common refrigerator conditions of roughly 3° C.

'Ashley Jay' produces mostly short conic fruit like its parent 'Ruby June', while the fruit of '52L32' is a longer conical shape, often with mis-shaped fruit. The fruit of 'Ashley Jay' generally ripens evenly from the tip to the shoulders of the berry, resulting in a uniform light red color over the whole fruit. In contrast, the fruit of '52L32' has a more pronounced tip to top ripening pattern that can often be blotchy. The fruit of 'Ashley Jay' is mostly absent of creases and is generally smooth and has a firmness that is equal to its two parents. The glossiness of 'Ashley Jay' is closer to that of 'Ruby June' which has a higher gloss, rather than the lower gloss of '52L32'.

The data set forth for 'Ashley Jay' in Tables 1, 2, and 3 was collected in June 2021 from plants grown at a test plot in Moss Landing, Monterey County, Calif. Yield, size and % Brix data was used from the previous season (2020) at the same location. Color terminology where noted is in accordance with the Pantone Color Formula Guide GP 1201.

In Table 1, the observed characteristics of 'Ashley Jay' are set forth.

TABLE 1

Detailed Description of Characteristics of 'Ashley Jay'

| | |
|---|---|
| SPECIFICATION: | |
| Genus/Species | *Fragaria* X *ananassa* |
| Market Name | Strawberry |
| PARENTS: | |
| Female | 'Ruby June' (U.S. Plant Pat. No. 27,190) |
| Male | '52L32' (Unpatented) |
| PLANT: | |
| Type | Short Day |
| Growth Habit | Semi-upright |
| Foliage density | Moderate/high |
| Vigor | Moderate |
| Height | Average 36.9 cm; range 33 cm to 41 cm |
| Width | Average 51.5 cm; range 46 cm to 57 cm |
| Crowns | Multiple crowns produced throughout season |
| Disease tolerance | Test plots have shown tolerance to *Fusarium* |
| Disease susceptibility | Susceptible to *Botrytis* |
| LEAFLET: | |
| Width | Average 15.5 cm; range 13.5 cm to 16.7 cm |
| Color | Adaxial surface: Pantone 371 U<br>Abaxial surface: Pantone 7490 U |
| Pubescence | Medium density |
| Inter-vein blistering | Slight |
| Glossiness | Slight |
| Variegation | None |
| TERMINAL LEAFLET: | |
| Length | Average 95.9 mm; range 81 mm to 115 mm |
| Width | Average 88.4 mm; range 69 mm to 104 mm |
| Ratio Length to width | 1.08 |
| Margins | Crenate |
| Leaf shape | Obovate |
| Base shape | Cuneate |
| Cross-section shape | Slight concave |
| PETIOLE: | |
| Pubescence | Slight |
| Petiole color | Pantone 382 U |
| Petiole length | Average 28.1 cm; range 25 cm to 30.8 cm |
| Petiole diameter | Average 4.59 mm; range 3.72 mm to 5.81 mm |
| STIPULE: | |
| Anthocyanin coloration | Slight |
| Length | Average 15.42 mm; range 9.7 mm to 19.3 mm |
| Width | Average 8.8 mm; range 5.97 mm to 10.53 mm |
| Color | Pantone 374 C (top and bottom surfaces) |
| STOLON: | |
| Anthocyanin coloration | Present, moderate |
| Pubescence | Moderate, fine |
| Diameter | Average 3.7 mm; range 2.8 mm to 4.82 mm |
| Length to first daughter | Not measured; typically varies from 25 cm to 50 cm |
| INFLORESCENCE: | |
| Flowering time | Moderately early |
| Position | Mostly at canopy |
| Number of blooms | Average 4.2; range 3 to 6 |
| Length | Average 33.6 cm; range 27 cm to 42 cm |
| Flower diameter | Average 25.8 mm; range 22.4 mm to 29.1 mm |
| Petal arrangement | Mostly overlapping |
| Petal number | Average 5.9; range 5 to 8 |
| Petal length | Average 12.4 mm; range 9.74 mm to 15.28 mm |
| Petal width | Average 12.3 mm; range 9.24 mm to 14.93 mm |
| Ratio Length to width | 1.01 |
| Petal color top surface | Pantone 11-4202 TPX |
| Petal color lower surface | Pantone 11-0601 TPX (bright white) |

TABLE 1-continued

Detailed Description of Characteristics of 'Ashley Jay'

| | |
|---|---|
| Calyx | Larger than the corolla |
| Calyx color | Adaxial Pantone 371 U<br>Abaxial Pantone 7490 U |
| Number of Sepals | Average 11; range 10 to 12 |
| Sepal length | Average 16.6 mm; range 13.9 mm to 20.2 mm |
| Sepal width | Average 8.79 mm; range 5.5 mm to 12.6 mm |
| Sepal top color | Pantone 371 U |
| Sepal bottom color | Pantone 7490 U |
| Sepal shape | Mostly elliptic |
| Sepal apex margin | Mostly entire, few lacerate |
| Stamens | Average 24.7; range 22 to 28 |
| Pedicel | Attitude of hairs is perpendicular to upright |
| FRUIT: | |
| Bearing | Short day, but remontant in cool coastal climates |
| Shape | Conic |
| Size | Seasonal average: 25 g |
| Fruit length | Average 48.9 mm; range 46.2 mm to 52.3 mm |
| Fruit diameter | Average 37.7 mm; range 34.7 mm to 40.7 mm |
| Achenes | Slightly below fruit surface |
| Glossiness | Medium |
| External color | Pantone 187 C |
| Internal color | Pantone 179 C |
| Evenness of external color | Even |
| Width of band at top devoid of achenes | Small |
| Yield | Approximate grams per plant: 1,199 g |
| Firmness | Medium, similar firmness to parent 'Ruby June' |
| % Brix | Seasonal average: 10.4; range 8 to 12.3 |

The comparison statistics set forth in the following Tables are with respect to characteristics observed at mid-season of 'Ashley Jay'. All measurements for 'Ashley Jay' were taken at a test plot in Moss Landing, Monterey County, Calif. during mid-season 2021. In Tables 2 and 3, the characteristics of 'Ashley Jay' are compared with historical data of the day neutral variety 'Sweet Ann' (U.S. Plant Pat. No. 22,472) and short-day variety 'Lucia' (U.S. Plant Pat. No. 26,974). Color identifications where noted herein are in accordance with the Pantone Color Formula Guide.

Plants and Foliage

The form and structure of the plants of 'Ashley Jay' are slightly shorter to that of 'Lucia' and 'Sweet Ann' plants. The plant spread of 'Ashley Jay', however, is wider than that of either 'Sweet Ann' or 'Lucia'. The canopy of 'Ashley Jay' is slightly denser than that of 'Sweet Ann' and 'Lucia'. The leaf surface of 'Ashley Jay' is also less blistered than that of 'Lucia' and more closely resembling that of 'Sweet Ann'. The glossiness of the leaves of 'Ashley Jay' is also less glossy than that of 'Lucia' and more similar to that of 'Sweet Ann'.

In Table 2, comparative data for foliar characteristics are presented for 'Ashley Jay' and historical data of two comparison cultivars, 'Sweet Ann' and 'Lucia'.

TABLE 2

Foliar Characteristics of 'Ashley Jay' Compared to 'Lucia' and 'Sweet Ann'

| Foliar | | Cultivar | | |
|---|---|---|---|---|
| Characteristics | | 'Lucia' | 'Sweet Ann' | 'Ashley Jay' |
| Plant height (mm) | Average | 391 | 380 | 369 |
| | Range | 292-490 | 290-480 | 330-410 |

TABLE 2-continued

Foliar Characteristics of 'Ashley Jay' Compared to 'Lucia' and 'Sweet Ann'

| Foliar Characteristics | | Cultivar 'Lucia' | 'Sweet Ann' | 'Ashley Jay' |
|---|---|---|---|---|
| Plant spread (mm) | Average | 472 | 420 | 515 |
| | Range | 430-550 | 330-510 | 460-570 |
| Leaf width (mm) | Average | 195 | 165 | 152 |
| | Range | 165-220 | 130-195 | 135-167 |
| Mid-tier leaflet length (mm) | Average | 103 | 88 | 96 |
| | Range | 82-116 | 72-105 | 81-115 |
| Mid-tier leaflet width (mm) | Average | 91 | 67 | 88 |
| | Range | 73-102 | 52-88 | 69-104 |
| Petiole length (mm) | Average | 268 | 220 | 281 |
| | Range | 230-355 | 150-280 | 250-308 |
| Petiole diameter (mm) | Average | 4.48 | 3.74 | 4.59 |
| | Range | 3.70-5.80 | 3.01-4.29 | 3.72-5.81 |
| Number leaflets per leaf | | 3 | 3 | 3 |
| Leaf convexity | | Slight concave | Slight concave | Slight concave |
| Shape leaflet base | | Rounded to obtuse | Obtuse | Cuneate |
| Leaf pubescence | | Medium density | Medium density | Medium density |
| Petiole pubescence | | Medium density | Medium density | Slight |
| Stipule length (mm) | Average | 35.74 | Not available | 15.42 |
| | Range | 30.2-39.7 | Not available | 9.7-19.3 |
| Stipule anthocyanin coloration | | Yes | Weak yes | Slight |
| Leaf margins | | Serrate to crenate | Commonly crenate | Crenate |
| Leaf color adaxial surface | | 364 U | 364 U | 371 U |
| Leaf color abaxial surface | | 363 U | 370 U | 7490 U |
| Petiole color | | 366 U | 383 U | 382 U |
| Leaf surface blistering | | Medium | Very weak | Slight |
| Leaf surface glossiness | | High | Medium | Slight |

Flowers and Fruit

'Ashley Jay' is a short-day variety that has ever bearing or remontant tendencies under certain temperature and horticultural conditions. This has been seen where plants grown in a cool coastal climate have continuously flowered throughout the growing season, while in nursery production in Manteca where summer temperatures are hot, there is no continuous flowering. While on average, 'Ashley Jay' has slightly longer inflorescences than 'Lucia' and 'Sweet Ann', when compared to their individual plant size all three varieties produce flowers that are at or above the canopy level, leaving flowers exposed to pollinators. The light red exterior color of the fruit of 'Ashley Jay' is similar in color to that of 'Lucia' and 'Sweet Ann', however while 'Sweet Ann' often has an unripe shoulder, no such shoulder exists in fruit of 'Ashley Jay' where it ripens nearly up to the calyx. The fruit of 'Ashley Jay' has good culinary qualities, including a good conic shape, good size, lighter red color, and an exceptional, sweet strawberry flavor.

In Table 3, comparative data for flower and fruit characteristics for 'Lucia', 'Sweet Ann' and 'Ashley Jay' are set forth.

TABLE 3

Flower and Fruit Characteristics of 'Ashley Jay' Compared to 'Lucia' and Sweet Ann'

| Characteristic | | Cultivar 'Lucia' | 'Sweet Ann' | 'Ashley Jay' |
|---|---|---|---|---|
| Petal number | | 5 | 5-6 | 5-8 |
| Petal length (mm) | Average | 12.44 | 11.21 | 12.39 |
| | Range | 10.6-14.3 | 9.2-13.13 | 9.74-15.28 |
| Petal width (mm) | Average | 11.86 | 11.05 | 12.27 |
| | Range | 10-13.1 | 9.0-13.1 | 9.24-14.93 |
| Position of flower (relative to foliage) | | most exposed | most exposed some even | most even |
| Pedicel length (mm) | Average | 430 | 330 | 336 |
| | Range | 380-540 | 240-420 | 270-422 |
| Sepal color (adaxial) | | 364 U | 364 U | 371 U |
| Sepal color (abaxial) | | 371 U | 370 U | 7490 U |
| Flower diameter (mm) | Average | 28.18 | 30.34 | 25.8 |
| | Range | 23.5-34.2 | 27.03-32.94 | 22.4-29.1 |
| Fruit color (external) | | 1788 C | 185 C | 187 C |
| Fruit color (internal) | | 179 C | 1788 C | 179 C |

Leaf samples from 'Ashley Jay', along with several proprietary selections from the breeding program including 'Lucia', 'Sweet Ann', 'Ruby June', 'Emilia' (U.S. Plant Pat. No. 30,427), 'Camila' (U.S. Plant Pat. No. 30,326), 'Sangria' (U.S. Plant Pat. No. 30,426), 'Scarlet' (U.S. Plant Pat. No. 27,034), and 'Sierra' (U.S. Plant Pat. No. 33,284), were submitted to a lab for allelic fingerprint comparison to the over two hundred other varieties of strawberry in its data base. The allelic fingerprint analysis establishes that 'Ashley Jay' is distinct and unique compared to the lab's large database of allelic fingerprints. While 'Ashley Jay' has equivalent alleles to other varieties for some individual markers, when looked at with several markers, a unique fingerprint is established.

Table 4 below sets forth the test results of three markers.

TABLE 4

Allelic Fingerprint Analysis

| Cultivar | M1 | M2 | M3 |
|---|---|---|---|
| 'Camila' | 204, 206, 224, 229 | 190, 232 | 279, 281, 289 |
| 'Emilia' | 204, 206, 214, 229 | 190, 232 | 279, 281, 289 |
| 'Lucia' | 202, 204, 206, 229 | 188, 216, 232 | 279, 281, 289 |
| 'Ruby June' | 206, 224, 229 | 188, 190, 216, 232 | 279, 289 |
| 'Sangria' | 204, 206, 229 | 190, 216 | 279, 289 |
| 'Scarlet' | 204, 206, 214, 229 | 173, 190, 232 | 279, 281, 289 |
| 'Sierra' | 204, 206, 229 | 232 | 279, 289 |
| 'Sweet Ann' | 204, 206, 229 | 190, 216, 232 | 279, 281, 289 |
| 'Ashley Jay' | 206, 224, 229 | 188, 216, 232 | 279, 281, 289 |

We claim:

1. A new and distinct strawberry plant named 'Ashley Jay' as described and illustrated by the characterizations set forth above.

* * * * *